United States Patent [19]

Aldridge

[11] Patent Number: 4,772,790

[45] Date of Patent: Sep. 20, 1988

[54] NON-DISPERSIVE OPTICAL GAS ANALYZER

[75] Inventor: Roland H. Aldridge, Los Angeles, Calif.

[73] Assignee: Teledyne Industries, Inc., Los Angeles, Calif.

[21] Appl. No.: 919,893

[22] Filed: Oct. 14, 1986

[51] Int. Cl.[4] .......... G01J 5/16

[52] U.S. Cl. .......... 250/343; 250/349

[58] Field of Search .......... 250/343, 344, 345, 346, 250/349; 374/124, 129, 179; 136/224, 225

[56] References Cited

U.S. PATENT DOCUMENTS

| | | | |
|---|---|---|---|
| 3,792,275 | 2/1974 | Leftwich et al. | 250/344 |
| 3,829,693 | 8/1974 | Schwarz | 250/344 |
| 4,514,635 | 4/1985 | Ishida et al. | 250/344 |
| 4,558,342 | 12/1985 | Sclar | 136/225 |
| 4,667,105 | 5/1987 | Miyatake et al. | 250/338 |

OTHER PUBLICATIONS

Szeles, Donald M., "A Simple DC Radiometer", Application Brief 1, Jul. 1978, Dexter Research Center.

Szeles, Donald M., "Temperature Compensation of DC Radiometers", Application Brief 2, Jul. 1978, Dexter Research Center.

Szeles, Donald M., "Emissivity Correction for Radiometers", Application Brief 3, Jul. 1978 Dexter Research Center.

Szeles, Donald M., "Blackbody Calculations Using a Programmable Calculator", Application Brief 4, Jul. 1978, Dexter Research Center.

Szeles, Donald M., "Variations in Calibration of Radiometers Using Cuton Optical Fillers", Application Brief 5, Jul. 1978, Dexter Research Center.

*Primary Examiner*—Carolyn E. Fields

*Assistant Examiner*—John A. Miller

*Attorney, Agent, or Firm*—Stephen L. King; Ronald W. Reagin

[57] ABSTRACT

A non dispersive optical gas analyzer is disclosed which uses thermopiles as optical detectors. The thermopiles are formed of an array of interconnected thin films of dissimilar metals deposited on a heat conductive substrate to form a multitude of thermocouples. The array is configured in such a manner that a number of the thermocouples are employed to compensate each thermopile output signal for changes in ambient temperature.

5 Claims, 5 Drawing Sheets

NON-DISPERSIVE OPTICAL GAS ANALYZER

BACKGROUND OF THE INVENTION

This invention relates to gas analyzers and, more particularly, to a non-dispersive optical gas analyzer which employs multiple thermopiles as optical energy detectors.

A wide variety of non-dispersive infrared gas analyzers have been developed over the years for measuring gas concentrations in applications such as medical and pollution monitoring and industrial process control. Examples of such analyzers are disclosed in U.S. Pat. No. 3,932,754, issued Jan. 13, 1976 to M. J. Riedl, et al; U.S. Pat. No. 4,069,420, issued Jan. 17, 1978 to T. C. Ross; and U.S. Pat. No. 4,420,687, issued Dec. 13, 1983 to M. S. Martinez, et al and assigned to the assignee of the present invention.

A common feature among prior art gas analyzers of the type referred to above is the use of a single infrared detector which detects infrared radiation in the form of a train of pulses of optical energy. These pulses represent, alternately, a measure of the infrared energy absorbed by a particular gas in a sample gas mixture, and the infrared energy absorbed by a reference gas. Suitable electronic circuitry processes the detector signals, which are also in the form of a pulse train, to produce a signal proportional to the concentration of the particular gas in the sample.

The alternating pulses of optical energy are generally provided by a motor-driven chopper wheel having apertures therein. Rotation of the wheel in conjunction with the aperture placement relative to a radiation source yields the desired alternating pulses.

A primary reason for employing the alternating pulse operation is to be able to use a single detector to measure both the sample and reference gases. Prior art designs have been limited to the use of a single infrared detector because, heretofore, it has not been possible to provide multiple detectors having sufficiently closely matched performance characteristics to yield an analyzer having the required accuracy.

For example, infrared sensors are highly sensitive to small changes in ambient temperature, and the responses of two separate detectors to such changes are not necessarily the same. Thus, it has proven extremely difficult to implement a multi-detector gas analyzer capable of providing accurate measurements under conditions of changing ambient temperature, without resorting to expensive, complicated and often unreliable temperature compensating devices and circuitry.

The need for a motor-driven chopper wheel in prior art analyzers has resulted in analyzer designs which are necessarily large, require substantial amounts of power to operate, and are intolerant of high levels of shock and vibration.

Accordingly, it is an object of the present invention to provide a new and improved non-dispersive optical gas analyzer.

It is another object of the invention to provide a non-dispersive optical gas analyzer which is small in size, exhibits low power consumption, and does not require a motor-driven chopper wheel for its operation.

It is yet another object of the invention to provide a portable, low cost, highly accurate non-dispersive optical gas analyzer employing multiple optical detectors and which is operable over a wide spectrum of wavelengths from the infrared to the ultraviolet.

SUMMARY OF THE INVENTION

The foregoing and other objects of the invention are accomplished by a non-dispersive optical gas analyzer including a radiation source for providing a directed beam of optical energy, and a generally cylindrical cell for containing the sample gas, one or more components of which are to be analyzed to determine their concentration in the mixture. To sample one gas component in the mixture, the analyzer employs two optical detectors, one a reference detector and the other a sample detector, to sense the optical energy after it has passed through the sample gas cell.

Each detector is in the form of a thermopile comprising a multitude of thermocouple junctions, each of which generates a thermal EMF proportional to the junction temperature. The thermopiles are made up of rows of thin films of dissimilar metals deposited on a heat conducting substrate. A portion of each thermopile is shielded from the optical energy exiting the cell. The shielded portion of each thermopile is used to compensate the thermopile output signal for changes in ambient temperature.

A first filter is placed between the cell and the unshielded portion of the sample thermopile to limit the wavelength of the optical energy impinging upon that portion of the thermopile to a range at which the optical energy is absorbed by the one component of gas in the sample mixture.

A second filter is placed between the cell and the unshielded portion of the reference thermopile to limit the wavelength of the optical energy impinging upon that portion of the thermopile to a reference wavelength range.

Control circuitry is employed to subtract the reference thermopile signal from the sample thermopile signal, and to divide the subtraction result by the reference thermopile signal.

Other objects, features and advantages of the invention will become apparent by reference to the specification taken in conjunction with the drawings in which like elements are referred to by like reference designations throughout the several views.

DESCRIPTION OF THE PREFERRED EMBODIMENT

Figure 1:
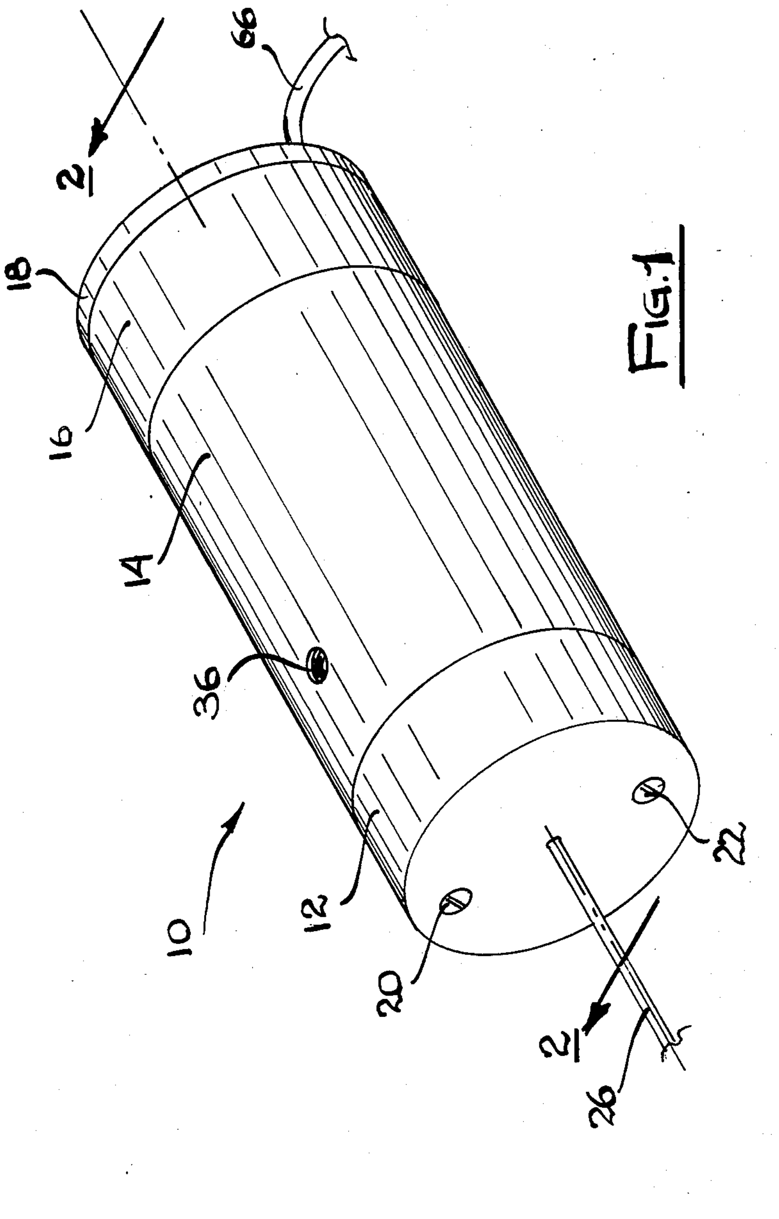
FIG. 1 is a perspective view showing a gas analyzer constructed in accordance with the teachings of the present invention.

FIG. 1 is a perspective view of a gas analyzer 10 constructed in accordance with the present invention. The analyzer 10 is made up of generally cylindrical sections 12, 14, 16, 18, held together by bolts which pass through holes in the sections and hold them in intimate contact.

Figure 2:
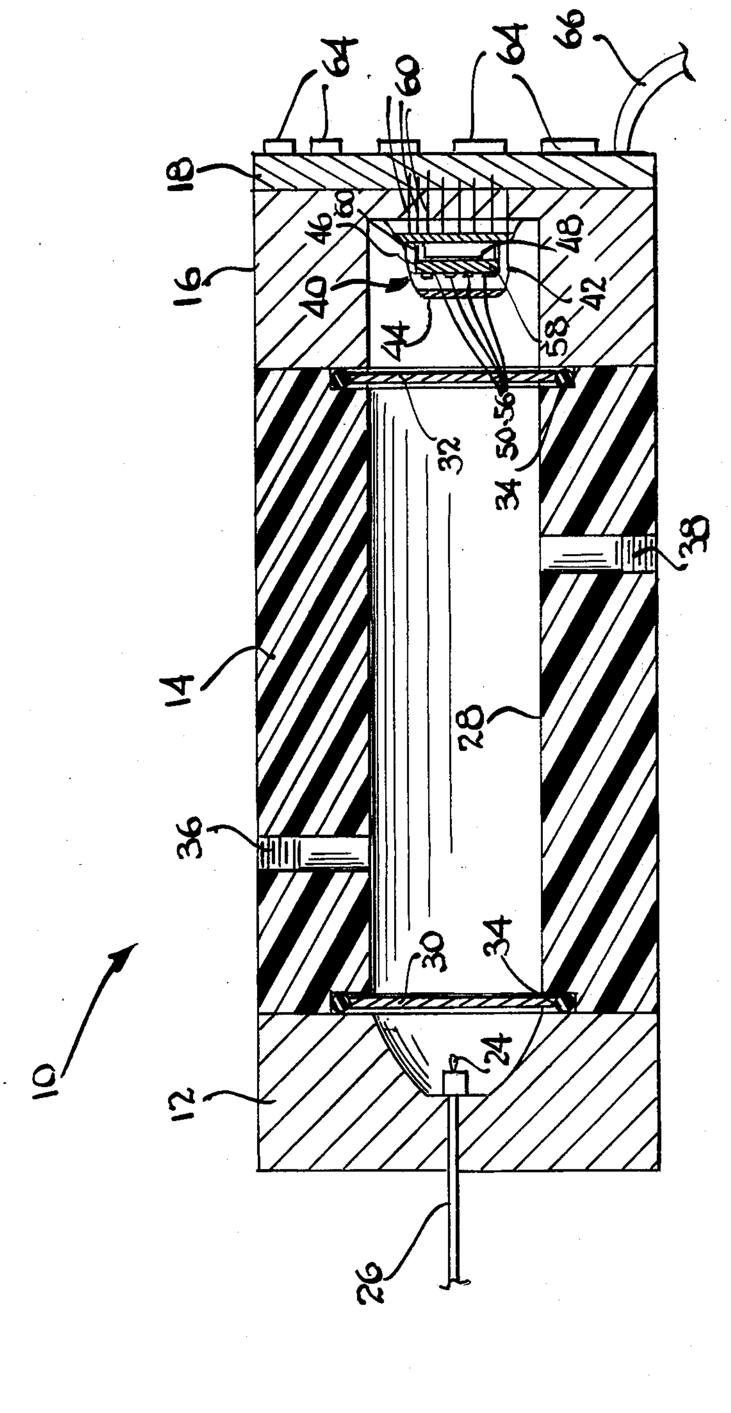
FIG. 2 is a cross-sectional view taken along the line 2—2 of FIG. 1, showing the internal arrangement of the components of the analyzer of FIG. 1.

FIG. 2 is a cross-sectional view of the analyzer 10, taken along the line 2—2 of FIG. 1. The section 12, which may be made of aluminum or the like, is used to support a radiation source 24 which may be in the form of a platinum wire bead or the like. A cable 26 is used to connect the wire bead 24 to an external power source such as batteries. When thus connected, the bead provides a source of optical energy. The portion of the section 12 surrounding the bead 24 is shaped as a parabolic reflector to direct the optical energy toward the adjacent end of section 14.

Section 14, which may be made of plastic or the like, includes a generally cylindrical cell 28 to contain the sample gas mixture to be analyzed. Windows 30, 32 are provided at the entrance and exit ends of the cell 28 and are held in place by O-rings 34 to form a gas tight enclosure. The windows may be formed of a material such as sapphire which is substantially transparent to the optical energy from source 24 over the range of wavelengths to be used for analyzing the gas mixture. An inlet 36 and outlet 38 are provided in the cell 28 to enable the sample gas to enter and exit the cell 28.

Section 16, which is formed of a heat conducting material such as aluminum, brass, stainless steel or the like, is mounted adjacent the exit end of the cell 28. The section 16 is used to mount an optical detector assembly 40 which is used to measure the optical energy exiting the cell 28.

The detector assembly 40 is housed in a generally cylindrical metal can 42 similar to those used to house transistors. One type of such enclosure is known as a TO-8 housing to those skilled in the art. The housing 42 is fitted with a transparent window 44 which may be sapphire or the like. Within the housing 42 is a planar substrate 46, about ten millimeters in diameter, made of a heat-conductive insulator such as beryllium or aluminum oxide. On one side of the substrate 46 is located an array 48 of four thermopiles formed by interconnecting lines of dissimilar thin-film metals deposited on the substrate surface. Thermopiles of this type are manufactured by Dexter Research Center, Inc., Dexter, Mich.

On the other side of the substrate 46, which faces the window 32 of cell 2, are located four filters 50, 52, 54, 56 which are positioned so that only selective wavelengths of optical energy exiting the cell 28 are passed through the heat-conductive substrate 46 to predetermined areas of the thermopile array 48. The remaining portion of this side of the substrate is covered with an optical masking material 58 such as aluminum which effectively prevents the optical energy which exits the cell 28 from being passed through the substrate 46 in those areas where the material 58 is located.

The substrate 46 is supported by conductive leads 60 which are partially embedded in, and pass through a header 62. The header 62, formed of epoxy or other suitable material, serves to close off the bottom of the housing 48 to form a gas-tight assembly 40. The space between the substrate 46 and the header 62 may be filled with a heat conductive material such as epoxy or the like to increase the thermal conductivity between these two elements. The leads 60 provide electrical connections to the thermopile array 42. The metal housing 42 is firmly attached to the heat conducting section 16, which has a thermal mass substantially greater than that of the housing 42 so that it acts as a large area heatsink to reduce the rate of change of temperature of the assembly 40 in response to a rapid change in analyzer ambient temperature.

The leads 60 pass through openings in the assembly 16 and are connected to conductive pads in the section 18, which is in the form of a printed circuit board. The board 18 includes electronic components 64 which process the voltages generated by the thermopile array 48 to provide signals representing the concentration of one or more gas components in the sample gas mixture. A cable 66 is used to provide power to the circuits and to connect the circuit output signals to suitable display apparatus.

Figure 3:
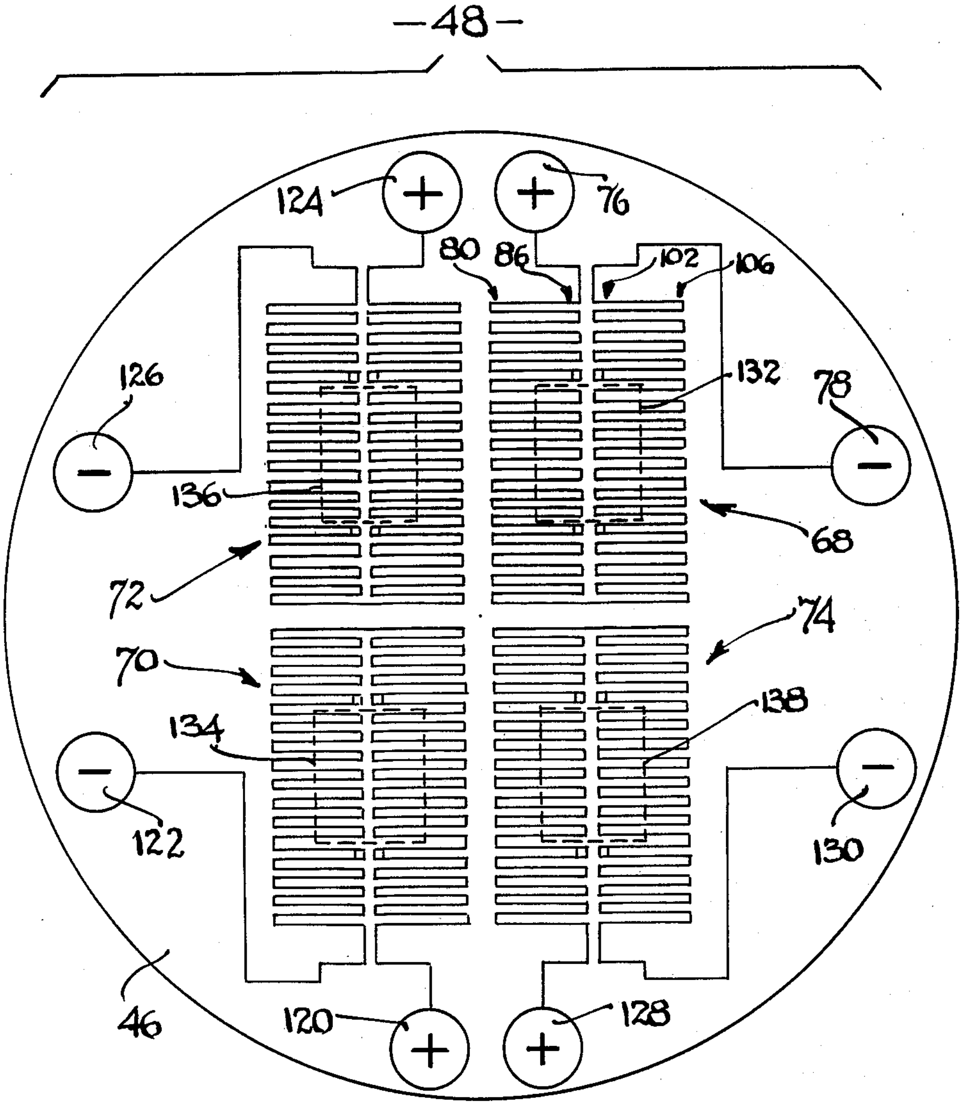
FIG. 3 is a side view of a heat conducting substrate supporting a plurality of thermopiles used as optical energy detectors in the gas analyzer of FIG. 1.

FIG. 3 is a side view of the substrate 46 showing in detail the construction of the thermopile array 48. The array 48 includes four thermopiles 68, 70, 72, 74. Each thermopile cconsists of a multitude of thermocouple junctions, each of which generates a thermal EMF proportional to the temperature of the junction. Each junction is formed by connecting together thin lines of dissimilar metals. The lines of metal are deposited on the surface of the substrate using thin-film deposition techniques well known to those skilled in the art. One advantage of using thermocouples as optical energy detectors is that they respond to steady state levels of radiation over a broad range of wavelengths extending from the infrared to the ultraviolet. To illustrate the construction of each thermopile, the thermopile 68 will be described in detail.

Figure 3A:
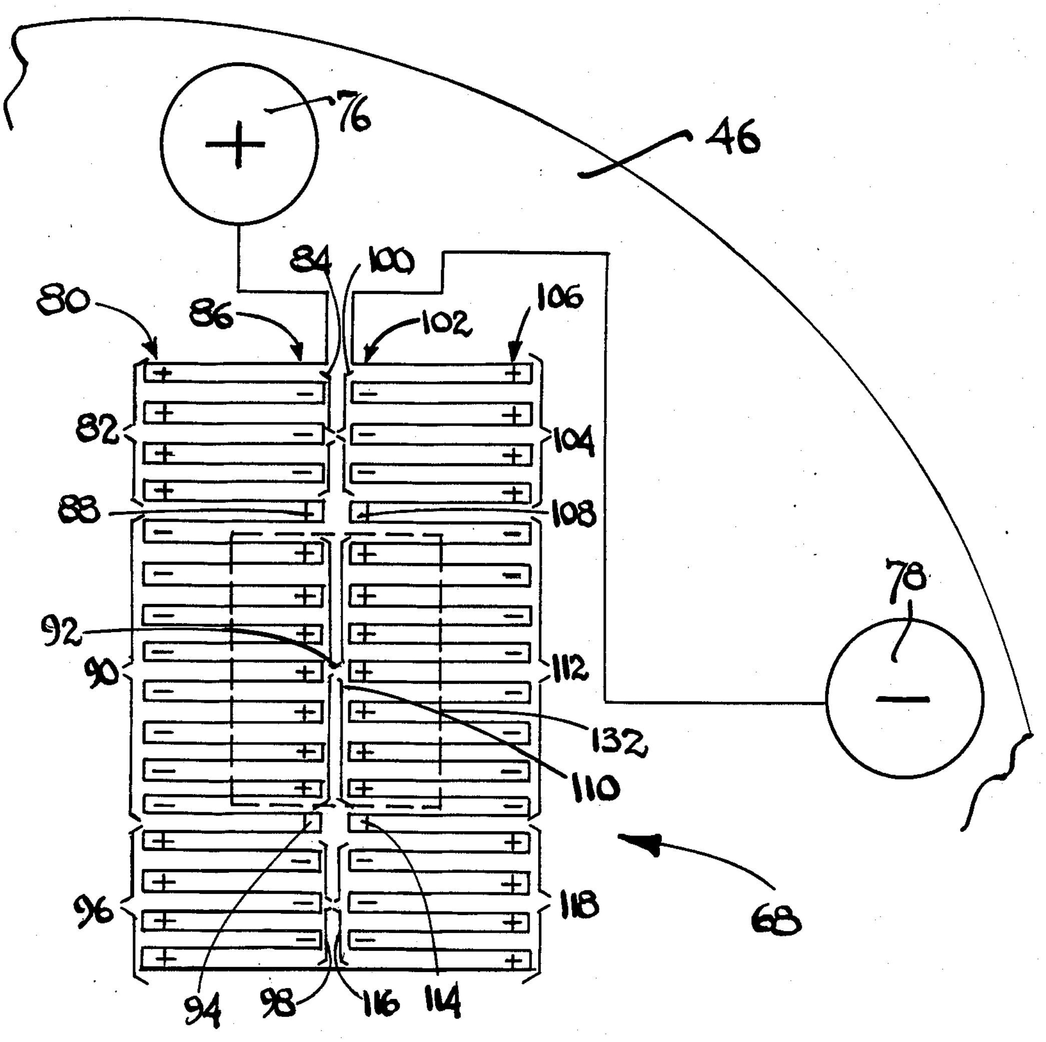
FIG. 3A is an enlarged fragmentary detail of the upper right quadrant of the substrate of FIG. 3.

As shown in FIGS. 3 and 3A the thermopile 68 includes a multitude of metal lines which are joined to adjacent lines at their ends (using, for example, a pod of noble metal such as gold) in a daisy-chain fashion to form a long series circuit terminating in terminals 76 and 78. The metals in adjoining lines are, for the most part, dissimilar from each other. For example, bismuth metal lines can be alternated with antimony metal lines. Where these lines join at their ends, thermocouple junctions are formed. In referring to the polarity of the thermal EMF generated by each thermocouple, terminal 76 will be taken as the positive reference with respect to terminal 78. The polarity established at each junction is determined by the arrangement of the lines of the two metals forming that junction. Accordingly, the polarity of a particular junction is established by the type of metal deposited in each of the lines in the thermopile.

The arrangement of the metal lines in the thermopile 68 is chosen to provide thermocouple junctions having the polarity indicated by the + and − symbols shown adjacent each junction in FIG. 3. It may be seen that the junctions are arranged as multiple rows in four columns. Beginning with left-most column 80, a first group 82 of four positive polarity thermocouple junctions is provided which are interconnected in series in an alternating fashion with a first group 84 of three negative polarity junctions in column 86 to form a first series circuit connected between the terminal 76 and a conductive pad 88 which may be formed of gold, silver, or the like. The column 86 is spaced apart beside and about 0.6 millimeters from the column 80.

A group 90 of eight negative polarity junctions which follow the group 82 in column 80 are series interconnected with a group 92 of seven positive polarity junctions which follow the group 84 in column 86 to form a second series circuit connected between the pad 88 and a pad 94 of similar construction. A group 96 of four positive polarity junctions which follow the group 90 in column 80 are series interconnected with a group 98 of three negative polarity junctions which follow the group 92 in column 86 to form a third series circuit connected between the pad 94 and the last row of metallization in the column 80.

A group 100 of three negative polarity thermocouple junctions is provided in a column 102 which is beside and closely adjacent to the column 86. The group 100 junctions are series interconnected with a group 104 of four positive polarity junctions in a column 106 spaced apart about 0.6 millimeters beside column 102, to form a fourth series circuit connected between terminal 78 and a pad 108 similar to pad 88.

A group 110 of seven positive polarity junctions following the group 100 in row 102 are series interconnected with a group 112 following the group 104 in column 106 to form a fifth series circuit connected between pad 108 and a pad 114 similar to pad 88. A group 116 of three negative polarity junctions following group 110 in column 102 is series interconnected with a group 118 of four positive polarity junctions following group 112 in column 106 to form a sixth series circuit connected between pad 114 and the bottom row of metallization extending from the group 96 junctions in the third series circuit.

From the above description, it may be seen that the first through sixth series circuits in the thermopile 68 are in turn series connected to form one long thermopile circuit between the terminals 76 and 78. The construction of the thermopiles 70, 72 and 74 is similar to the construction of the thermopile 68. Thus the thermopile 70 is in the form of a series interconnection of thermocouple junctions, organized in a four-column array, which terminate at terminals 120 and 122. In like manner, the series circuit comprising the thermopile 72 terminates at terminals 124 and 126 and the series circuit comprising the thermopile 74 terminates at terminals 128 and 130. The polarity symbols in FIG. 3 indicate the various thermocouple junction polarities in the thermopiles 70, 72, 74 in a manner analogous to that for the thermopile 68.

The active portion of each thermopile 68, 70, 72, 74, which is responsive to the optical energy to be measured, is shown by dotted lines 132, 134, 136, 138, respectively, in FIG. 3. It may be seen that this active area is restricted to the positive polarity thermocouple junctions in the center two columns of each thermopile. Thus, for the thermopile 68, the active area is restricted to the junction groups 92 and 110.

The thermopile active areas are established using the masking material 58 previously described. This masking material is provided as a covering or coating on the side of the substrate 46 opposite to the thermopile side. The coating covers substantially all of that side of the substrate behind the thermopile array 48 except for the areas directly behind the dotted areas 132–138. The masking material 58 prevents the optical energy which exits the cell 28 from passing through those portions of the heat conducting substrate 46 covered by the material 58 to those portions of the array 48 located directly behind the material 58 on the opposite side of the substrate 46.

Using the thermopile 68 as an example, (see FIG. 3A) the thermocouple junction groups 82, 84, 90, 96, 98, 100, 104, 112, 116, and 118 are shielded by the masking material, leaving only the groups 92 and 110 able to sense optical energy passing through the substrate 46 from the cell 28. The ten groups of junctions shielded by the masking layer are used to temperature compensate the signal produced by the thermopile 68 for changes in the temperature of the substrate 46 as caused by changes in the ambient temperature of the analyzer 10.

Since the thermopiles 68–74 are used to provide voltage signals which are a measure of the amount of optical energy, at predetermined wavelengths, exiting from the sample gas cell 28, it is important that the voltage signals are not materially affected by changes in ambient temperature, since these changes introduce measurement error. It has been found that changes in ambient temperature produce a nonlinear temperature gradient across the surface of the substrate 46. Such a gradient can produce substantial error in the voltage produced by the active thermocouple groups which, ideally, should respond only to the optical energy exiting the cell 28.

It has also been found that by surrounding the active thermocouple junction groups in each thermopile with temperature compensating groups in the arrangements shown in FIG. 3, the nonlinear temperature effects caused by ambient temperature changes can be compensated for by the voltages generated by these compensating groups.

Further, the actual number of thermocouple junctions in each of the twelve groups in a thermopile may be determined as a result of empirical or experimental analysis of the non-linear temperature gradient across the substrate 46 in order to more precisely compensate for temperature changes. Accordingly, the number of junctions in a particular group may vary in each thermopile depending on the location of the thermopile on the substrate 46. Thus, while each of the thermopiles 68–74 in FIG. 3 are shown as having the same number of junctions in corresponding groups, the invention is by no means limited to that configuration.

Each of the thermopiles 68–74 is used to sense optical energy over a particular range of wavelengths as it exits the cell 28. The particular wavelength range to be sensed by each thermopile is based on the particular gas component to be analyzed in the mixture. One of the four thermopiles, for example the thermopile 70, is made responsive to a wavelength range which does not coincide with the wavelengths at which optical energy is absorbed by any of the gas components to be analyzed in the mixture. As indicated below, this particular thermopile 70 is designated as the reference thermopile.

The remaining three thermopiles 68, 72, 74, designated as sample thermopiles, are each used to sense radiation at a wavelength at which a particular gas component is absorbed in the mixture. Thus, the three thermopiles are capable of providing signals for analysis of three gas components. Obviously, if it is desired to analyze only one gas component in the mixture, a single sample thermopile, in addition to the reference thermopile, is all that is necessary.

The wavelength of optical energy reaching each thermopile is restricted to the desired range by mounting the four optical bandpass filters 50–56, previously described, on the side of the substrate 46 opposite to that on which the array 48 is mounted, where each filter 50, 52, 54, 56 covers an area corresponding to the dotted areas 132, 134, 136 and 138 in FIG. 3.

By way of example, if the analyzer 10 is to be used to analyze three components of automobile exhaust gas, such as $CO_2$, CO and NO, using, respectively, the thermopiles 68, 72 and 74, the filter 50, covering the area 132 would be chosen to have a central wavelength of about 4.27 microns and a bandwidth of about 110 nanometers, corresponding to $CO_2$ absorption; the filter 54, covering the area 136 would be chosen to have a central wavelength of 4.77 microns and a bandwidth of about 100 nanometers, corresponding to CO absorption; and the filter 56, covering the area 138 would be chosen to have a central wavelength of 2.85 microns and a bandwidth of about 170 nanometers corresponding to NO absorption. The filter 52, covering the area 132 of the reference thermopile 68, may be chosen to have a central wavelength of 4.0 microns and a bandwidth of about 240 nanometers, corresponding to a wavelength range which does not cross over into the absorption spectra of any of the other components to be analyzed in the mixture.

While the filters 50–56 need only cover the active areas 132–138, respectively, these filters, which are made from thin sheets of material such as germanium or potassium bromide are typically made larger than the active area. The larger size makes it easier to fabricate the filters, which are generally cut from large sheets. The larger size also enables the edges of the filter, which may be slightly chipped from the cutting operation, to be located outside the active area.

The operation of the analyzer 10 described thus far is as follows. Referring to FIG. 1, power is provided to radiation source 24, whereby optical energy is directed by reflector 12 through the cell 28, previously filled with the sample gas mixture. The optical energy exiting the cell 28 through window 32 impinges on the side of the substrate 46 containing the masking layer 58 and the filters 50–56.

The masking layer 58 prevents the optical energy from reaching any but the active areas 132–138 of the thermopile array 48 located on the opposite side of the substrate 46. The filters 50–56, on the other hand, pass only selective wavelengths of the optical energy to the respective active areas 132–138.

The thermopiles 68–74 each generate a voltage related to the amount of optical energy sensed by their respective active area, while the other areas of each thermopile compensate the thermopile voltage for changes in ambient temperature. The temperature compensated thermopile voltages which appear at the terminal pairs 76–78, 120–122, 124–126, and 128–130 are provided as input signals to control circuitry which operates in the following manner.

Figure 4:
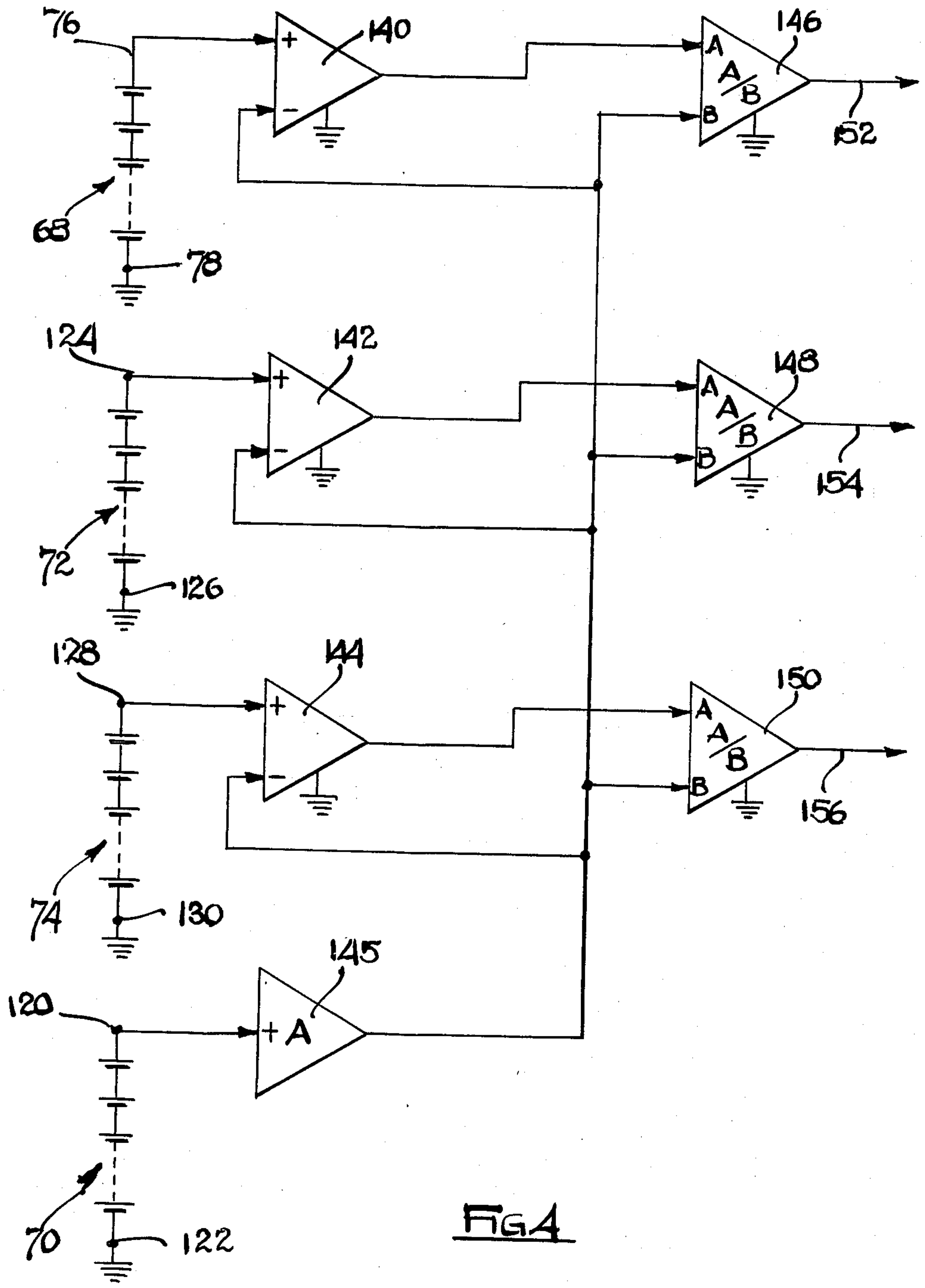
FIG. 4 is a schematic/block diagram of control circuits used to process the voltages generated by the thermopiles to provide indications of gas concentration.

Referring to FIG. 4, the signals from the thermopiles 68, 72, and 74 are provided through leads 60 from detector assembly 40 to the positive input terminals of differential amplifiers 140, 142 and 144, respectively. It is envisioned that these amplifiers provide adjustable offset and gain factors for each input signal. These amplifiers are located on the printed circuit board 18, derive their power through cable 66 and measure signals with respect to the ground terminals shown. The signal from the reference thermopile 70 is provided through a scaling amplifier 145 to the negative input terminals of all three amplifiers 140, 142, 144, and is also provided to the divisor input terminals of three arithmetic division elements 146, 148, 150. These division elements 146–150 also derive their power through the cable 66, are mounted on the board 18, and measure signals with respect to the ground terminals shown.

The output terminals of the amplifiers 140, 142 and 144 are connected, respectively, to the dividend input terminals of the division elements 146, 148, and 150. From the above description of the circuits shown in FIG. 4, it will be apparent that each of the signals from the sample thermopiles 68, 72, 74 has subtracted from it the signal from the reference thermopile 70. The result of each subtraction is in turn divided by the signal from the reference thermopile 70. The result of each division appears as an output signal at output terminals 152, 154 and 156 of the division circuits 146, 148 and 150, respectively. It may be shown that the signals appearing at these output terminals are directly related to the concentration of the gas components corresponding to the absorption spectra of the respective filters 50, 54, 56 described above.

The signals on the lines 152, 154 and 156 may be provided to display and recording apparatus after suitable filtering and linearizing in a manner well known to those skilled in the art. Many other circuits may be employed to perform the functions described above. For example, it is contemplated that a microprocessor element may be employed to perform the arithmetic functions.

While the invention is disclosed and a particular embodiment is described in detail, it is not intended that the invention be limited solely to this embodiment. Many modifications will occur to those skilled in the art which are within the spirit and scope of the invention. It is thus intended that the invention be limited in scope only by the appended claims.

What is claimed is:

1. A gas analyzer comprising:

radiation generating means for providing a directed beam of optical energy;

a generally cylindrical cell for containing a gaseous mixture, at least one component of which is to be analyzed to determine its concentration in the mixture and having first and second ends transparent to the optical energy;

a first thermopile comprising a multitude of thermocouple junctions, each of which generates a thermal EMF proportional to the temperature of the junction and including:

a first plurality of thermocouple junctions, arranged in rows in a first column;

a second plurality of thermocouple junctions arranged in rows in a second column which is located beside the first column;

a third plurality of thermocouple junctions arranged in rows in a third column which is located beside the second column;

a fourth plurality of thermocouple junctions arranged in rows in a fourth column which is located beside the third column;

first connecting means for connecting a first group of A rows of thermocouple junctions in the first column in series with a first group of B rows of thermocouple junctions in the second column to form a first series circuit such that the thermal EMF generated by each of the first A rows of junctions is of a common polarity which is opposite to the polarity of the thermal EMF generated by each of the first B rows of junctions;

second connecting means for connecting a second group of C rows which follow the A rows of thermocouple junctions in the first column in series with a second group of D rows which follow the B rows of thermocouple junctions in the second column to form a second series circuit such that the thermal EMF generated by each of the C rows of junctions is of a common polarity which is opposite to the polarity of the thermal EMF generated by each of the A and D rows of junctions;

third connecting means for connecting a third group of E rows which follow the C rows of thermocouple junctions in the first column in series with a third group of F rows which follow the D rows of junctions in the second column to form a third series circuit such that the EMF generated by each of the E rows of junctions is of a common polarity which is opposite to the polarity of the EMF generated by each of the C and F rows of junctions;

fourth connecting means for connecting a first group of G rows of thermocouple junctions in the third column in series with a first group of H rows of thermocouple junctions in the fourth column to form a fourth series circuit such that the thermal EMF generated by each of the G rows of junctions is of a common polarity which is opposite to the polarity of the thermal EMF generated by each of the first A and H rows of junctions;

fifth connecting means for connecting a second group of I rows which follow the G rows of thermocouple junctions in the third column in series with a second group of J rows which follow the H rows of thermocouple junctions in the fourth column to form a fifth series circuit such that the thermal EMF generated by each of the I rows of junctions is of a common polarity which is opposite to the polarity of the thermal EMF generated by each of the C and J rows of junctions;

sixth connecting means for connecting a third group of K rows which follow the I rows of thermocouple junctions in the third column in series with a third group of L rows which follow the J rows of junctions in the fourth column to form a sixth series circuit such that the EMF generated by each of the K rows of junctions is of a common polarity which is opposite to the polarity of the EMF generated by each of the E and L rows of junctions;

seventh connecting means for connecting the first through sixth series circuits together in series to form a first thermopile series circuit such that the A, D, E, H, I and L rows of junctions are connected in a series-adding configuration;

a second thermopile comprising a multitude of thermocouple junctions, each of which generates a thermal EMF proportional to the temperature of the junction and including:

a fifth plurality of thermocouple junctions, arranged in rows in a fifth column;

a sixth plurality of thermocouple junctions arranged in rows in a sixth column which is located beside the sixth column;

a seventh plurality of thermocouple junctions arranged in rows in a seventh column which is located beside the sixth column;

an eighth plurality of thermocouple junctions arranged in rows in an eighth column which is located beside the seventh column;

eighth connecting means for connecting a first group of M rows of thermocouple junctions in the fifth column in series with a first group of N rows of thermocouple junctions in the sixth column to form a seventh series circuit such that the thermal EMF generated by each of the first M rows of junctions is of a common polarity which is opposite to the polarity of the thermal EMF generated by each of the first N rows of junctions;

ninth connecting means for connecting a second group of O rows which follow the M rows of thermocouple junctions in the fifth column in series with a second group of P rows which follow the N rows of thermocouple junctions in the sixth column to form an eighth series circuit such that the thermal EMF generated by each of the O rows of junctions is of a common polarity which is opposite to the polarity of the thermal EMF generated by each of the M and P rows of junctions;

tenth connecting means for connecting a third group of Q rows which follow the O rows of thermocouple junctions in the fifth column in series with a third group of R rows which follow the P rows of junctions in the sixth column to form a ninth series circuit such that the EMF generated by each of the Q rows of junctions is of a common polarity which is opposite to the polarity of the EMF generated by each of the O and R rows of junctions;

eleventh connecting means for connecting a first group of S rows of thermocouple junctions in the seventh column in series with a first group of T rows of thermocouple junctions in the eighth column to form a tenth series circuit such that the thermal EMF generated by each of the S rows of junctions is of a common polarity which is opposite to the polarity of the thermal EMF generated by each of the M and T rows of junctions;

twelfth connecting means for connecting a second group of U rows which follow the S rows of thermocouple junctions in the seventh column in series with a second group of V rows which follow the T rows of thermocouple junctions in the eighth column to form an eleventh series circuit such that the thermal EMF generated by each of the U rows of junctions is of a common polarity which is opposite to the polarity of the thermal EMF generated by each of the O and V rows of junctions;

thirteenth connecting means for connecting a third group of W rows which follow the U rows of thermocouple junctions in the seventh column in series with a third group of X rows which follow the V rows of junctions in the eighth column to form a twelfth series circuit such that the EMF generated by each of the W rows of junctions is of a common polarity which is opposite to the polarity of the EMF generated by each of the Q and X rows of junctions;

fourteenth connecting means for connecting the seventh through twelfth series circuits together in series to form a second thermopile series circuit such that the M, P, Q, T, U and X rows of junctions are connected in a series-adding configuration;

thermopile mounting means for locating the first and second thermopiles on a common heat conducting substrate;

positioning means for positioning the radiation generating means, the cell and the thermopile substrate so that the beam of optical energy is directed axially through the cell to the firt and second thermopiles;

masking means for shielding the A, B, C, E, F, G, H, J, K and L rows of thermocouple junctions in the first thermopile and the M, N, O, Q, R, S, T, V, W, and X rows of thermocouple junctions in the second thermopile from the beam of optical energy exiting the cell;

first filter means positioned between the cell and the D and I rows of thermocouple junctions in the first thermopile for limiting the wavelength of the optical energy which impinges upon the D and I rows of junctions to a range at which the optical energy is absorbed by the one component of gas in the gas mixture;

second filter means positioned between the cell and the P and U rows of thermocouple junctions in the second thermopile for limiting the wavelength of the optical energy which impinges upon the P and U rows of junctions to a reference wavelength range;

control means to measure the EMF generated by the first thermopile series circuit representing a first signal related to the amount of optical energy impinging on the D and I rows of junctions, to measure the EMF generated by the second thermopile series circuit representing a second signal related to the amount of optical energy impinging on the P and U rows of junctions, to subtract the first signal from the second signal, to produce a third signal, and to divide the third signal by the second signal.

2. The analyzer of claim 1 in which the numbers of thermocouple junctions in each of rows A, H, E and L are equal to each other, the numbers of thermocouple junctions in each of rows C and J are equal to each other, the numbers of thermocouple junctions in each of rows D and I are equal to each other, and the numbers of thermocouple junctions in each of rows B, G, F and K are equal to each other.

3. The analyzer of claim 1 in which the numbers of thermocouple junctions in each of rows M, T, Q and X are equal to each other, the numbers of thermocouple junctions in each of rows O and V are equal to each other, the numbers of thermocouple junctions in each of rows P and U are equal to each other, and the numbers of thermocouple junctions in each of rows N, S, R and W are equal to each other.

4. The analyzer of claim 1 in which the thermocouple junctions are formed of connected thin films of dissimilar 5. A gas analyzer comprising: a cell for containing a gaseous mixture;

means for transmitting a directed beam of optical energy through the cell;

a plurality of thermopiles each positioned to receive a portion of the directed beam of optical energy, each of the thermopiles comprising a substrate and a plurality of series-connected thermocouples comprising dissimilar thin-film metals deposited on the substrate in two columns, the thermocouples in each column lying parallel to each other, each column being divided into a center and two end sections of thermocouples, the thermocouples in the center section being arranged to have a first polarity and the thermocouples in the end sections being arranged to have a polarity opposite the first polarity, all of the sections of a column being connected in series, the total of thermocouples in the two end sections of each column being approximately equal to the number of thermocouples in the center section, each column of thermocouples being connected in series to the other column, and the thermocouples of each section of each column being positioned with polarities which are the mirror-image of the polarities of the adjacent section in the adjacent column of the same thermopile;

means for selectively transferring optical energy of selected wavelengths to only the adjacent ends of the thermocouples of the central sections of each column in each thermopile; and means for comparing signals generated by at least two of the thermopiles to determine the components of a gaseous mixture in the cell.

* * * * *

UNITED STATES PATENT AND TRADEMARK OFFICE
CERTIFICATE OF CORRECTION

PATENT NO. : 4,772,790

DATED : 9-20-88

INVENTOR(S) : Aldridge

It is certified that error appears in the above-identified patent and that said Letters Patent is hereby corrected as shown below:

| Column | Line | Correction |
|---|---|---|
| 3 | 45 | delete "2", insert --28-- |
| 3 | 59 | delete "48", insert --42-- |
| 3 | 64 | delete "42", insert --48-- |
| 12 | 2 | delete "dissimilar", insert --dissimilar metals deposited on the substrate-- |

Signed and Sealed this

Eighteenth Day of July, 1989

*Attest:*

DONALD J. QUIGG

*Attesting Officer*

*Commissioner of Patents and Trademarks*